United States Patent [19]

Güthlein et al.

[11] 4,385,114
[45] May 24, 1983

[54] OXIDATION INDICATORS COMPRISING 3,3',5,5'-TETRAALKYLBENZIDINE COMPOUNDS

[75] Inventors: Werner Güthlein, Mannheim-Neckarau; Walter Rittersdorf, Mannheim-Waldhof; Hugo Tiedemann, Mannheim-Wallstadt; Peter Vogel, Weinheim; Wolfgang Werner, Mannheim-Vogelstang, all of Fed. Rep. of Germany

[73] Assignee: Boehringer Mannheim GmbH, Mannheim, Fed. Rep. of Germany

[21] Appl. No.: 236,487

[22] Filed: Feb. 23, 1981

Related U.S. Application Data

[63] Continuation of Ser. No. 851,579, Nov. 15, 1977, abandoned, which is a continuation of Ser. No. 777,194, Mar. 14, 1977, abandoned, which is a continuation of Ser. No. 635,534, Nov. 26, 1975, abandoned.

[30] Foreign Application Priority Data

Dec. 21, 1974 [DE] Fed. Rep. of Germany ....... 2460903

[51] Int. Cl.³ .................... C12Q 1/28; C12Q 1/26; C12Q 1/60; C12Q 1/62
[52] U.S. Cl. .................................. 435/28; 435/10; 435/11; 435/14; 435/25; 435/805; 436/95; 436/135; 436/810
[58] Field of Search ............. 435/10, 11, 14, 28, 435/805, 25, 810; 23/230 B; 252/408; 436/95, 135, 810

[56] References Cited

U.S. PATENT DOCUMENTS

| | | | |
|---|---|---|---|
| 2,290,436 | 7/1942 | Kamlet | 23/230 B |
| 3,413,197 | 11/1968 | Fraser | 435/14 |
| 3,418,083 | 12/1968 | Rey et al. | 435/28 |
| 3,627,697 | 12/1971 | Rey et al. | 435/14 |
| 3,630,847 | 7/1968 | Rey et al. | 435/14 |
| 3,770,381 | 11/1973 | Schmitt et al. | 435/28 |
| 3,926,732 | 12/1975 | Rosen et al. | 435/27 |

FOREIGN PATENT DOCUMENTS 818344 7/1969 Canada.

OTHER PUBLICATIONS

Holland et al., Tetrahedron, 30, 3299–3302 (1974).

*Primary Examiner*—Esther M. Kepplinger
*Attorney, Agent, or Firm*—Felfe & Lynch

[57] ABSTRACT

The detection and determination of (a) hydrogen peroxide or of a substance which reacts with the formation of hydrogen peroxide or (b) of peroxidase or a peroxidatively active substance, is carried out by contacting an unknown sample with a chromogen and, in case (a), with a peroxidatively active substance or in case (b) with hydrogen peroxide or a substance which reacts with the formation of hydrogen peroxide, and evaluating the coloration produced by the reaction, wherein, as the chromogen, there is used at least one 3,3',5,5'-tetraalkylbenzidine compound of the formula:

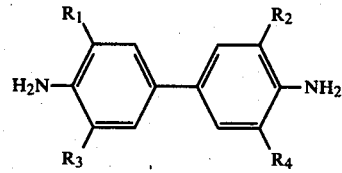

wherein $R_1$, $R_2$, $R_3$ and $R_4$, which can be the same or different, are straight-chained or branched alkyl radicals containing up to 6 and preferably up to 4 carbon atoms.

23 Claims, No Drawings

OXIDATION INDICATORS COMPRISING 3,3',5,5'-TETRAALKYLBENZIDINE COMPOUNDS

This is a continuation of Ser. No. 851,579 filed Nov. 15, 1977 now abandoned, which, in turn is a continuation of Ser. No. 777,194 filed Mar. 14, 1977, now abandoned which in turn is a continuation of Ser. No. 635,534 filed Nov. 26, 1975, now abandoned.

The present invention is concerned with oxidation indicators which contain 3,3',5,5'-tetraalkylbenzidine compounds. In addition, the invention comprehends a process for the determination of hydrogen peroxide (and of substances which liberate hydrogen peroxide) as well as for the determination of peroxidase and of peroxidatively active substances.

The reaction of hydrogen peroxide with oxidation indicators, catalyzed by peroxidase or peroxidatively active materials to give colored compounds, is of particular importance in analytical chemistry because, apart from the detection of hydrogen peroxide and of peroxidases, it can also be used for the determination of a series of materials which react with oxygen and an oxidase with the formation of hydrogen peroxide. In the following, there are given several examples of such materials, with the appropriate oxidases thereafter in brackets: glucose (glucose oxidase), galactose (galactose oxidase), L-amino acids (L-aminoacid oxidase), cholesterol (cholesterol oxidase) and uric acid (uricase). The materials in question are, in particular, those, the detection and determination of which are of great importance in medical diagnosis and in foodstuff chemistry.

As detection reaction for peroxidases, the method for the determination of hemoglobin is of particular importance in which, instead of hydrogen peroxide, organic hydroperoxides can also be used as oxidation agents.

Due to their great importance in rapid medical diagnosis, so-called rapid tests have been described for all of the above-mentioned reactions which permit a qualitative or quantitative determination of individual reaction components. Absorbent carriers or films are thereby used which contain all the reagents and in the case of which, after contact with the liquid to be investigated, a color reaction takes place when the substance in question is present. The color formed is assessed with the help of color comparison tables or is measured with a remission photometer so that from the color intensity there can be deduced the concentration of the reacting substance.

Numerous compounds have been described in the literature and in patent specifications as oxidation indicators for these rapid tests but few of them have actually been used in practice. The indicators in question are almost exclusively compounds of the benzidine series and, of these, in particular o-tolidine. In spite of the wide use of this indicator and of its undoubted advantages in comparison with other known indicators, nevertheless o-tolidine suffers from certain disadvantages. On the one hand, this compound does not always have an optimum stability in the formulations used for the rapid tests, which can lead to undesired colorations and losses of sensitivity after comparatively long periods of storage. On the other hand, the blue-green radical cations resulting from the indicator reactions are not very stable because, due to further oxidation, these cations are converted relatively easily into the brown quinodiimine. Therefore, the reaction colors have, due to this subsidiary brown color, in some cases a dirty appearance and furthermore, the colors change quickly and are, therefore, even only a short time after the recommended reading off time, often no longer capable of correct evaluation. In the case of serial analyses and for record purposes, this is a decisive disadvantage. The radical cations can admittedly be stabilized to a certain extent with anionic wetting agents but these cannot always be used since they can have a destabilizing effect on the oxidases used for the primary reaction.

Surprisingly, we have now found that rapid tests of the above-described type can be obtained, which are more storage stable and give more stable colored radicals when proceeding according to the instant invention.

The invention provides the use, instead of o-tolidine, of at least one 3,3',5,5'-tetraalkylbenzidine of the general formula

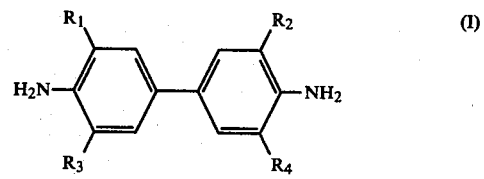

wherein $R_1$, $R_2$, $R_3$ and $R_4$ which can be the same or different, are straight-chained or branched alkyl radicals containing up to 6 and preferably up to 4 carbon atoms.

The present invention thus provides a process (a) for the detection and determination of hydrogen peroxide, or of substances which react with the formation of hydrogen peroxide, or (b) of peroxidases or the peroxidatively active substances by contacting the unknown sample with a chromogen and, in case (a) with a peroxidatively active substance or, in case (b) with hydrogen peroxide (or a substance which reacts with hydrogen peroxide) and evaluating the coloration produced by the reaction, wherein, as chromogen, there is used at least one 3,3,5,5'-tetraalkylbenzidine of general formula (I).

The present invention also provides a diagnostic agent for the determination of hydrogen peroxide or of substances which react with the formation of hydrogen peroxide, comprising peroxidase or a peroxidatively active substance and a chromogen of general formula (I), as well as a diagnostic agent for the determination of hemoglobin or of other peroxidatively active substances, comprising hydrogen peroxide or a substance forming hydrogen peroxide and a chromogen of general formula (I). These diagnostic agents can be in the form of, for example, a solution or a test paper or a test film.

Processes for the preparation of some of the compounds of the general formula (I) are known although hitherto only 3,3',5,5'-tetramethylbenzidine (V. R. Holland et al., Tetrahedron, 30, 3299-3302/1974) and 3,3',5,5'-tetraethylbenzidine (R. Stroh et al., Angew. Chem., 69, 124-131/1957) have been characterized. The preparation of 3,3',5,5'-tetramethylbenzidine according to Holland et al. (loc. cit.) is carried out by reducing the known 2,3',6,6'-tetramethylazobenzene with zinc dust, followed by a benzidine rearrangement.

3,3'Dimethyl-5,5'-diethylbenzidine and 3,3',5,5'-tetraisopropylbenzidine, which have hitherto not been described, can be prepared, for example, by the method described by Stroh et al. (loc cit.) from o-tolidine and ethylene or from benzidine and propylene, respectively.

Other methods which, in principle, can also be used for the higher alkyl derivatives, which have hitherto not been described, are the following:

(a) oxidatica of 2,6-dialkylanilines with alkaline ferricyanide (cf. V. R. Holland, loc.cit.; G. Schulz, Ber. dtsch. chem. Ges., 17, 476–478/1884; E. Haselbach, Helv. chim. Acta, 53, 1526–1543/1970);

(b) oxidation of 2,6-dialkylanilines with silver (II) oxide (cf. B. Ortiz et al., J. Org. Chem., 37, 2748–2750/1972);

(c) reduction of 2,6-dialkylnitrobenzenes with lithium aluminium hydride (cf. R. F. Nystrom and H. C. Brown, J.A.C.S., 70, 3738–3740/1948);

(d) reaction of 2,6-dialkylbenzene-diazonium salts with an ammoniacal cuprous solution (cf. D. Vorlander and F. Mayer, Liebigs Ann. Chem., 320, 122–144/1902).

The further reduction of the azobenzenes obtained in this manner and their, in some cases, simultaneous benzidine rearrangement takes place according to known methods (e.g., as described in Houben-Woyl, X/2, 705–724 and X/1, 839–848).

The suitability, to be expected in principle from the structure, of 3,3',5,5'-tetramethylbenzidine for the detection of occult blood in faeces and urine is described in the above-mentioned references from Holland et al., in which the advantage, in comparison with tolidine, of having a low cancerogeneity is particularly stressed. However, the unexpectedly greater stability of this amine and of its radical cation in rapid tests is not described by Holland since he did not carry out appropriate experiments for this purpose. Indeed, there was no reason to carry out such experiments since the users of rapid tests do not handle them directly and thus the question of cancerogeneity was of practically no importance.

Some of the compounds of general formula (I) have also been described for rapid tests for the detection of halides and pseudo-halides in body fluids (see Canadian Pat. No. 818,344). These rapid tests also contain cupric compounds which react with the halides with the formation of cuprous halides and free halogen which, in turn, oxidizes the benzidine compounds. This oxidation apparently leads to the same colored radical cations as the peroxidase-catalyzed oxidation with hydroperoxides. In the above-mentioned Canadian patent specification, of the numerous benzidine derivatives disclosed therein, o-tolidine (3,3'-dimethyl-benzidine) is preferred, from which it is to be deduced that the tetraalkylbenzidines are less suitable for rapid tests.

The comparatively great stability of the compounds of general formula (I) and of their radical cations is also surprising insofar as the electron-repelling influence of the additional alkyl radicals rather pointed towards an increased oxidizability and thus would have led to the expectation of a further reaction of the radical cations to the brown quinonediimine.

The tetraalkylbenzidines used according to the present invention can be employed in all cases in which o-tolidine has previously been employed, possibly with somewhat modified formulations. Anionic wetting agents used for color stabilization can be replaced by less active ones or even omitted entirely. Thus, the tetraalkylbenzidines can be used, for example, in test papers for the detection of glucose in urine, of blood in urine, of cholesterol in serum and of hydrogen peroxide in milk or in test films for the determination of glucose in blood and serum and in many other tests. All these tests are characterized in that the color reactions are more luminescent, more stable and, in some cases, better graduated than in the case of the use of o-tolidine since the blue-green to green colorations of the radical cations of the tetraalkylbenzidines are not "dirtied" by brown quinonediimines.

In the rapid tests described in the following Examples, the properties of the tetraalkylbenzidines used according to the present invention can be particularly well seen, individual representatives of this class of compounds possibly also having especially advantageous actions: thus, the increased storage-stability of the tetraalklbenzidines of general formula (I), in comparison with o-tolidine, shows itself especially in the case of the storage of test papers for the detection of blood in urine. The increased stability of the radical cations leads, in the case of test films for the determination of glucose, to the fact that the measurement can be carried out over a relatively long period of time. The use of tetraalkylbenzidines for testing for glucose in urine gives test papers in which the reaction colors remain almost unchanged for days on end which, for early recognition reactions in which the test subject sends the used test strips to a central point for evaluation, is of particular importance.

The following Examples are given for the purpose of illustrating the present invention.

EXAMPLE 1

Preparation of test paper for the detection of blood in urine

Filter paper (Schleicher and Schüll No. 23SL) was successively impregnated with the following solutions and dried at 40° C.:

| Solution 1 | |
|---|---|
| 1.2 molar citrate buffer of pH 5.25 | 35.0 ml. |
| ethylenediamine-tetraacetic acid disodium salt | 0.1 g. |
| dioctyl sodium sulphosuccinate | 0.5 g. |
| 2,5-dimethylhexane-2,5-dihydroperoxide (about 70%) | 1.6 g. |
| phosphoric acid trimorpholide | 12.7 g. |
| ethanol | 30.0 ml. |
| distilled water | ad 100.0 ml. |
| Solution 2 | |
| 3,3',5,5'-tetramethylbenzidine | 0.3 g. |
| phenanthridine | 0.2 g. |
| toluene | ad 100.0 ml. |

A white test paper was obtained which, upon dipping into a blood-containing urine, becomes blue-green after about 5–20 seconds. If the erythrocytes were intact, then the papers were speckled blue-green. If hemolysis had taken place or if free hemoglobin was present ab initio in the urine, then the paper was uniformly blue-green colored. The sensitivity was about 5 erythrocytes/mm$^3$ or the corresponding amount of hemoglobin. A lower count of intact erythrocytes can, under certain circumstances, still bring about individual blue-green spots on the test paper. The sensitivity towards myoglobin corresponds to that for hemoglobin.

After keeping for 3 days at 60° C., the test papers were very pale yellowish colored but their sensitivity was essentially unchanged, merely the reaction times having lengthened to about 60–90 seconds. A test paper of the same composition but containing o-tolidine instead of the tetramethylbenzidine was, after the same temperature stressing, yellow-brown colored and the sensitivity was about 20 erythrocytes/mm³.

Papers of the same sensitivity and stability but which merely react somewhat more slowly and with a pure green color, were obtained by using equimolar amounts of 3,3',5,5'-tetraethyl-, 3,3'-dimethyl-5,5'-diethyl- or 3,3',5,5'-tetraisopropylbenzidine.

EXAMPLE 2

Preparation of test paper for the detection of blood in urine

When, in the formulation described in Example 1, the dioctyl sodium sulphosuccinate was replaced by the same amount of lauroyl sarcosine or when the surface-active agent was omitted entirely, then test papers were obtained which were admittedly less sensitive than those of Example 1 but which were still more sensitive than corresponding papers containing o-tolidine. The color reactions with a urine sample which contains 50 hemolyzed erythrocytes/mm³ were summarized in the following Table.

TABLE

| Indicator | without wetting agent | with lauroyl sarcosine as wetting agent |
|---|---|---|
| tetramethylbenzidine | pale green | green |
| o-tolidine | pale green-brown | pale brown-green |

EXAMPLE 3

Preparation of test paper for the detection of glucose in urine

Filter paper (Schleicher & Schüll 597 NF) was impregnated with solutions of the following composition and dried at 50° C.:

| Solution 1 | |
|---|---|
| glucose oxidase (70 U/g.) | 222 mg. |
| peroxidase (70 U/g.) | 28 mg. |
| morpholinoethane sulphonate buffer (pH 6: 1.0M) | 50 ml. |
| tartrazine | 80 mg. |
| polyvinyl pyrrolidine | 300 mg. |
| distilled water | ad 100 ml. |
| Solution 2 | |
| 3,3',5,5'-tetramethylbenzidine | 600 mg. |
| ethanol | ad 100 ml. |

Test papers were also produced in the same way which contain 3,3',5,5'-tetraethylbenzidine or o-tolidine. The reaction colors of these test papers with glucose-containing urine samples about 60 to 120 seconds after dipping in were summarized in the following Table. In the case of tetramethylbenzidine, these colors remain constant for about 10–15 minutes and, upon drying, they achieved a more bluish character and remained stable in this form for several days. The colors with tetraethylbenzidine became slightly paler upon drying, without the color value changing, and were then stable for several days. The colors obtained with o-tolidine already began to yellow after 5 to 10 minutes and also to become paler and, after drying, were, depending upon the glucose concentration, completely faded or pale olive brown in about 2 to 4 hours.

TABLE

| mg. % glucose | o-tolidine | Tetramethyl-benzidine | tetraethyl-benzidine |
|---|---|---|---|
| 0 | yellow | yellow | yellow |
| 50 | bright green | bright green | bright green |
| 100 | green | blue-green | medium green |
| 250 | blue-green | green-blue | green |
| 500 | green-blue | blue-black | dark green |
| 1000 | olive-black | black | deep green |

Test papers which contain an equimolar amount of 3,3'-dimethyl-5,5'-diethylbenzidine behaved, with regard to character and stability of the reaction colors, in practically the same way as those with tetraethylbenzidine.

EXAMPLE 4

Preparation of test papers for the detection of hydrogen peroxide

Filter paper was impregnated with the following solutions and dried at 40° C.:

| Solution 1 | |
|---|---|
| trisodium citrate dihydrate | 225 mg. |
| citric acid monohydrate | 175 mg. |
| peroxidase (70 U/g.) | 50 mg. |
| sodium alginate | 150 mg. |
| polyoxyethylene sorbitan monolaurate (Tween 20) | 1300 mg. |
| vinylpyrrolidine-vinyl acetate copolymer | 375 mg. |
| distilled water | ad 100 ml. |
| Solution 2 | |
| 3,3',5,5'-tetramethylbenzidine | 500 mg. |
| acetone | ad 100 ml. |

The test paper thus obtained gave, with hydrogen peroxide in aqueous solution, for example in milk, blue-green color reactions down to concentrations of 0.1 mg%.

Example 5

Preparation of test paper for the detection of cholesterol and of cholesterol esters in serum Filter paper (Schleicher & Schüll 597 NF, Ind.) is impregnated with solutions of the following composition and dried at 40° C.:

| Solution 1 | |
|---|---|
| 1M citrate buffer pH 7 | 20.0 ml. |
| cholesterol oxidase (60 U/mg.) | 0.1 g. |
| cholesterol esterase (18 U/mg.) | 0.25 g. |
| peroxidase (70 U/g.) | 0.05 g. |
| distilled water | ad 100.00 ml. |
| Solution 2 | |
| 3,3',5,5'-tetramethylbenzidine | 0.28 g. |
| polyethylene octyl phenol ether (Triton X 100) | 0.5 g. |
| methylene chloride | ad 100.0 ml. |

The test papers thus obtained reacted with sera which contain cholesterol and/or cholesterol esters with green color shades, the intensity of which corresponded to the concentration of the cholesterol. Corresponding test papers which, instead of tetramethylbenzidine, contain o-tolidine, also reacted with green color shades which were, however, less intensive.

Example 6

Preparation of test film for the determination of low glucose contents in blood or serum

| Components | |
|---|---|
| polyvinyl acetate propionate dispersion (Propiofan 70 D) | 45.0 g. |
| 1.85% solution of sodium alginate in 0.5M phosphate buffer of pH 5.5 | 35.0 g. |
| sodium nonyl sulfate dissolved in 5.0 ml. water | 0.75 g. |
| glucose oxidase (62.7 U/mg.) ⎫ dissolved in | 0.189 g. |
| peroxidase ⎬ 10 ml. water | |
| (68.8 U/mg.) ⎭ | 0.235 g. |
| 3.3',5,5'-tetramethylbenzidine dissolved in 5 ml. acetone | 0.68 g. |

The components were well mixed, coated on a foil with a layer thickness of 200μ and dried for 35 minutes at 60° C. Dropping on glucose-containing blood and wiping it off after 1 minute gave, after a further 2 minutes, in the range of 5 to about 100 mg.% glucose, blue-green reaction colors with increasing intensity which can be measured with a commercially-available remission photometer (Reflomat). The following Table shows the kinetics of the color development with 60 mg.% glucose in comparison with a test film in which, instead of the tetramethylbenzidine, there were present 500 mg. o-tolidine. If the test film is heated to 50° C. for 12 days, then practically no discoloration can be ascertained. On the other hand, a test film containing o-tolidine was very strongly yellow-brown colored.

TABLE

| time in minutes | 1 | 2 | 3 | 5 | 10 |
|---|---|---|---|---|---|
| intensity with tetramethylbenzidine | 88 | 87 | 85 | 84 | 85 |
| intensity with o-tolidine | 73 | 68 | 64 | 60 | 67 |

Example 7

Preparation of test film for the determination of normal and increased glucose content in blood or serum A test film was produced as described in Example 6 which additionally contained 0.050 g. 9-(γ-aminopropyl)-3-aminocarbazole dihydrochloride. Dropping on of glucose-containing blood and wiping it off after one minute gave, after a further minute, the following reaction colors:

60 mg.% glucose—ochre
120 mg.% glucose—olive
180 mg.% glucose—blue-green with increasing color depth.

Even after keeping for two days in the air in the laboratory, these colors did not change. In the case of an analogous film which contains 0.600 g. o-tolidine and 0.025 g. 9-(γ-aminopropyl)-3-aminocarbazole dihydrochloride, the blue-green colors changed in the direction of yellow-green shades.

The following Table shows the long-term stability of the colors obtained with 150 mg.% glucose, measured in a Reflomat:

TABLE

| Time in hours | 0 | 1 | 2 | 4 | 8 | 24 |
|---|---|---|---|---|---|---|
| tetramethylbenzidine | 61 | 62 | 62 | 62 | 62 | 62 |
| o-tolidine | 51 | 52 | 51 | 50 | 47 | 42 |

If the test film were heated to 50° C. for 12 days, then practically no discoloration can be ascertained and the evaluation on the basis of comparative colors was completely satisfactory. However, the o-tolidine-containing test strips were strongly yellow-brown discolored and a comparison with a color scale was no longer possible.

The following Examples describe the preparation of two new compounds of general formula (I):

Example 8

Preparation of 3,3'-dimethyl-5,5'-diethylbenzidine

Variant I

96.5 g. (0.564 mol) 2-methyl-6-ethyl-aniline hydrochloride were suspended in a mixture of 79.5 ml. concentrated hydrochloric acid (d.=1.18) and 330 ml. water in a 2 liter three-necked flask equipped with a stirrer, a dropping funnel and a thermometer. There was then added dropwise thereto, with good ice cooling, at 0°-3° C., a solution of 39 g. sodium nitrite in 150 ml. water, with stirring, within the course of 30 minutes. Stirring was thereafter continued for about 1 hour at 0°-3° C. and the diazonium salt solution obtained was diluted with 600 ml. ice water.

In the meantime, 210 g. cupric sulfate were dissolved in 900 ml. water in a 6 liter three-necked flask equipped with a stirrer, dropping funnel and thermometer (Y-piece) and mixed with 363 ml. concentrated ammonia (d.=0.88). 90 g. Hydroxyammonium chloride were dissolved in 150 ml. water and a solution of 95 g. potassium hydroxide in 72 ml. water were then added thereto dropwise, with ice cooling. This well cooled solution was added at 10°-15° C., under an atmosphere of nitrogen and within the course of 15 minutes, to the stirred copper tetramine solution, a bright blue cuprous salt complex thereby being formed. The cooled diazonium salt solution was added dropwise, with ice cooling, vigorous stirring and under an atmosphere of nitrogen at 12°-15° C. within the course of 1.5 hours (dropping funnel provided with inlet tube, which extends with a U-shaped bend below the surface of the copper salt solution). At the end of the addition, stirring was continued for one hour, whereafter the reaction solution was shaken out with 4×200 ml. diethyl ether. The combined ethereal extracts were shaken out with 3×50 ml. 25% aqueous sodium hydroxide solution, 2×100 ml. water, 3×100 ml. 2 N hydrochloric acid and 2×100 ml. water. 55.4 g. of azo compound was obtained in the form of a red oil. Chromatographic separation on a silica gel column (filling height 100 cm., column diameter 4.8 cm.) with chloroform-ligroin (1:4) (amount of silica 1.5 kg., particle diameter 0.062-0.2 mm.) gave 33.7 g. of pure 2,2'-dimethyl-6,6'-diethylazobenzene in the form of a red oil. This was dissolved in 1.6 liter diethyl ether, 330 ml. ethanol were added thereto and then a solution of 135 g. ammonium chloride in 1.5 liters water and 300 g. zinc dust were added thereto portionwise, with vigorous stirring, at 22° C. After stirring for 5 hours, the reduction was finished. The almost completely decolorized organic phase was separated off and the aqueous phase was shaken out three times with 250 ml. amounts of diethyl ether. The combined ethereal extracts were then mixed with 210 ml. 3 N sulfuric acid and stirred. The sulfate is thereby formed as a colorless, initially sticky precipitate. After the addition of 200 ml. ethanol, there were obtained 30.5 g. 3,3'-dimethyl-5,5'-diethylbenzidine sulfate in the form of colorless crystals. This product was introduced into 150 ml. boiling water, cooled to ambient temperature, mixed with 200 ml 2 N aqueous sodium hydroxide solution and extracted 4 times with 100 ml. amounts of chloroform. The combined chloroform extracts were dried over anhydrous sodium sulfate and evaporated. A residue of 25.5 g. of pale brown crystals was obtained. This crude product was recrystallized from aqueous methanol. There were obtained 23 g. (30.4% of theory) 3,3'-dimethyl-5,5'-diethylbenzidine in the form of beige-colored crystals with a melting point of 69°–70° C. The corresponding dihydrochloride ($C_{18}H_{24}N_2 \cdot 2HCl$) melts, with decomposition, at 289°–291° C.

Variant II 1.5 g. aluminum and 0.1 g. mercury chloride were heated with 75 g. aniline in an autoclave at 300° C., the aluminum thereby dissolving with the evolution of hydrogen. After cooling, 92 g. o-tolidine and 4.5 g. anhydrous aluminum chloride were added thereto. The reaction mixture was then heated to 280°–300° C. and ethylene forced in at 200 ats. The take up of ethylene is finished after about 3 hours. Thereafter, the reaction mixture was cooled and the reaction mass shaken out with a dilute aqueous solution of sodium hydroxide. 2-ethylaniline and 2,6-diethylaniline were distilled off from the organic phase in a vacuum (up to about 120° C./10 mm.Hg.). The residue was recrystallized several times from dilute hydrochloric acid. There was thus obtained the dihydrochloride of 3,3'-dimethyl-5,5'-diethylbenzidine which melts, with decomposition, at 288°–292° C.

Example 9

Preparation of 3,3', 5,5'-tetraisopropylbenzidine

A solution of 100 g. 2,6-diisopropylaniline in 1280 ml. water and 102 ml. concentrated hydrochloric acid (d.=1.18) was heated to 90° C. and rapidly added dropwise to a solution of potassium hexacyanoferrate (III) in 5100 ml. water and 143 g. sodium hydroxide with a temperature of 97° C. Because of the free hydrocyanic acid formed, the operation was carried out with efficient ventilation. The resultant red-colored suspension was further stirred for 15 minutes, cooled and shaken out 6 times with 300 ml amounts of diethyl ether. The ethereal extracts were dried over anhydrous sodium sulfate, filtered with suction and evaporated. There were obtained 97 g. of azo compound in the form of a red oil. Chromatographic separation on a silica gel column (filling height 110 cm., column diameter 8 cm.) with chloroform-ligroin (1:4) (amount of silica gel 1.5 kg., particle size 0.05–0.2 mm.) gave 32.45 g. brick-red crystals which melt at 134°–136° C.

The azo compound was dissolved in 500 ml. glacial acetic acid. 150 g. zinc dust were added thereto and the reaction mixture was heated under reflux for 30 minutes, while stirring. Thereafter, excess zinc dust was filtered off with suction and the solvent evaporated in a vacuum. There were obtained 17.5 g. of colorless crystals which were stirred with 150 ml. water. 150 ml. 2 N aqueous sodium hydroxide solution were added thereto and the mixture then shaken out three times with 150 ml. amounts of chloroform. There were thus obtained 12.4 g. crude 3,3', 5,5'-tetraisopropylbenzidine. This was mixed with 90 ml. acetic anhydride, briefly boiled and the excess acetic anhydride evaporated on a rotary evaporator. The residue obtained was dissolved in 20 ml. isopropanol, 180 ml. ligroin were added thereto and the crystals formed were filtered off with suction. The N,N'-diacetyl compound obtained was again recrystallized from isopropanol-ligroin (2:1). 7.6 g. colorless crystals were isolated, which have a melting point of 366° C. For the splitting off of the N-acetyl groups, these were heated in a mixture of 180 ml. glacial acetic acid and 50 ml. concentrated hydrochloric acid in an autoclave for 6 hours at 130°– 140° C. Thereafter, the reaction solution was evaporated, the residue was mixed with 300 ml. 2 M aqueous sodium hydroxide solution and the liberated base was extracted with 4×50 ml. chloroform. The chloroform extracts were dried over anhydrous sodium sulfate, filtered with suction and evaporated. There was thus obtained 3,3',5,5'-tetraisopropylbenzidine in the form of a brownish oil. The yield was 5.6 g. (M.W. 352). The corresponding dihydrochloride ($C_{24}H_{36}N_2 \cdot 2HCl$) melts, with decomposition, at 263°–265° C.

It will be understood that the specification and examples are illustrative but not limitative of the present invention and that other embodiments within the spirit and scope of the invention will suggest themselves to those skilled in the art.

What is claimed is:

1. Method for the determination of (a) hydrogen peroxide or of a substance which reacts with the formation of hydrogen peroxide or of (b) peroxidase or a peroxidatively active substance which comprises contacting an unknown sample with an absorbent carrier sequentially impregnated with first (i) a solution of, in case (a), peroxidase or a peroxidatively active substance dissolved in a water-containing solvent or, in case (b), hydrogen peroxide (or a substance which reacts with the formation of hydrogen peroxide) dissolved in a water-containing solvent and, secondly, (ii) a solution of a chromogen dissolved in an organic liquid containing solvent, and the absorbent carrier being dried after said sequential impregnation, and evaluating the coloration produced by the reaction, wherein, as the chromogen, there is used 3,3',5,5'-tetraalkylbenzidine compound of the formula

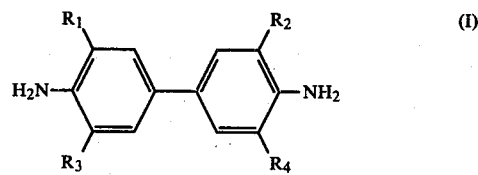

wherein $R_1$, $R_2$, $R_3$ and $R_4$, which can be the same or different, are straight-chained or branched alkyl radicals containing up to 6 carbon atoms.

2. Method as claimed in claim 1 for the determination of hydrogen peroxide or of a substance which reacts with the formation of hydrogen peroxide, which method comprises contacting an unknown sample with an absorbent carrier sequentially impregnated with, first, a water-containing solution of peroxidase or a peroxidatively active substance, and, secondly, an organic liquid containing a solution of a chromogen compound of formula (I), the absorbent carrier being dried after said sequential impregnation, and evaluating the coloration produced by the reaction as a measure of the presence of hydrogen peroxide or substance which reacts with the formation of hydrogen peroxide.

3. Method as claimed in claim 1 for the determination of a peroxidase or a peroxidatively active substance which method comprises contacting an unknown sample with an absorbent carrier sequentially impregnated with first, a water-containing solution of hydrogen peroxide or a substance which reacts with the formation of hydrogen peroxide and, secondly, an organic liquid containing a solution of a chromogen compound of formula (I), the absorbent carrier being dried after said sequential impregnation, and evaluating the coloration produced by the reaction as a measure of the presence of peroxidase or a peroxidatively active substance.

4. Method as claimed in claim 1 wherein $R_1$, $R_2$, $R_3$ and $R_4$ are individually selected from alkyl of up to 4 carbon atoms.

5. Method as claimed in claim 1 wherein said chromogen is 3,3'-dimethyl-5,5'-diethylbenzidine.

6. Method as claimed in claim 1 wherein said chromogen is 3,3',5,5'-tetraisopropylbenzidine.

7. Method as claimed in claim 1 wherein an anionic wetting agent is also impregnated into said absorbent carrier.

8. Method as claimed in claim 7 wherein said anionic wetting agent is dioctyl sodium sulphosuccinate.

9. Diagnostic composition for the determination of hydrogen peroxide or of a substance which reacts with the formation of hydrogen peroxide which composition comprises an absorbent carrier sequentially impregnated with first, a water-containing solution of peroxidase or a peroxidatively active substance and, secondly, an organic liquid containing solution of a chromogen compound of the formula $$\text{(I)}$$

$R_1$, $R_2$ on one ring; $R_3$, $R_4$ on other ring; $H_2N-$ and $-NH_2$ para substituents (biphenyl structure).

wherein
$R_1$, $R_2$, $R_3$ and $R_4$, which can be the same or different, are straight-chained or branched alkyl radicals containing up to 6 carbon atoms,
said absorbent carrier being dried after said sequential impregnations.

10. Diagnostic composition as claimed in claim 9 in the form of a test paper.

11. Diagnostic composition as claimed in claim 9 wherein said compound is 3,3'-dimethyl-5,5'-diethylbenzidine.

12. Diagnostic composition as claimed in claim 9 wherein said compound is 3,3',5,5'-tetraisopropylbenzidine.

13. Diagnostic composition as claimed in claim 9 wherein an anionic wetting agent is also impregnated into said absorbent carrier.

14. Diagnostic composition as claimed in claim 13 wherein said anionic wetting agent is dioctyl sodium sulphosuccinate.

15. Diagnostic composition for the determination of peroxidase or of a peroxidatively active substance which composition comprises an absorbent carrier sequentially impregnated with, first, a water-containing solution of hydrogen peroxide or of a substance which reacts with the formation of hydrogen peroxide, and, secondly, an organic liquid containing solution of a chromogen compound of the formula $$\text{(I)}$$

biphenyl structure with $R_1$, $R_2$, $R_3$, $R_4$ and $H_2N-$, $-NH_2$ groups.

wherein
$R_1$, $R_2$, $R_3$ and $R_4$, which can be the same or different, are straight-chained or branched alkyl radicals containing up to 6 carbon atoms,
said absorbent carrier being dried after said sequential impregnations.

16. Diagnostic composition as claimed in claim 15 in the form of a test paper.

17. Diagnostic composition as claimed in claim 15 wherein said compound is 3,3'-dimethyl-5,5'-diethylbenzidine.

18. Diagnostic composition as claimed in claim 15 wherein said compound is 3,3'5,5-tetraisopropylbenzidine.

19. Diagnostic composition as claimed in claim 15 wherein an anionic wetting agent is also impregnated into said absorbent carrier.

20. Diagnostic composition as claimed in claim 19 wherein said anionic wetting agent is dioctyl sodium sulphosuccinate.

21. Process for making a diagnostic composition for the determination of (a) hydrogen peroxide or of a substance which reacts with the formation of hydrogen peroxide or of (b) peroxidase or a peroxidatively active substance which comprises sequentially impregnating an absorbent carrier with first, (i) a solution of, in case (a), peroxidase or peroxidatively active substance dissolved in a water-containing solvent, or, in case (b), hydrogen peroxide (or a substance which reacts with the formation of hydrogen peroxide) dissolved in water-containing solvent and, secondly, (ii) a solution of a chromogen dissolved in an organic liquid containing solvent, and then drying the absorbent carrier after said sequential impregnation, wherein said chromogen is of the formula $$\text{(I)}$$

biphenyl structure with $R_1$, $R_2$, $R_3$, $R_4$ and $H_2N-$, $-NH_2$ groups.

wherein
$R_1$, $R_2$, $R_3$ and $R_4$, which can be the same or different, are straight-chained or branched alkyl radicals containing up to 6 carbon atoms.

22. Process as claimed in claim 21 for making a diagnostic composition for the determination of hydrogen peroxide or of a substance which reacts with the formation of hydrogen peroxide, which process comprises impregnating an absorbent carrier sequentially with, first, a water-containing solution of peroxidase or a peroxidatively active substance and, secondly, an organic liquid containing a solution of a chromogen compound of formula (I), and then drying the absorbent carrier after said sequential impregnation.

23. Process as claimed in claim 21 for making a diagnostic composition, for the determiantion of peroxidase or a peroxidatively active substance which process comprises sequentially impregnating an absorbent carrier with, first, a water-containing solution of hydrogen peroxide or a substance which reacts with the formation of hydrogen peroxide, and, secondly, an organic liquid containing solution of a chromogen compound of formula (I), and then drying the absorbent carrier after said sequential impregnation.

* * * * *